United States Patent
Sfeir et al.

(10) Patent No.: US 11,317,955 B2
(45) Date of Patent: May 3, 2022

(54) MAGNESIUM ENHANCED/INDUCED BONE FORMATION

(71) Applicant: UNIVERSITY OF PITTSBURGH—OF THE COMMONWEALTH SYSTEM OF HIGHER EDUCATION, Pittsburgh, PA (US)

(72) Inventors: Charles S. Sfeir, Wexford, PA (US); Amy Chaya, Strafford, PA (US); Andrew J. Brown, Pittsburgh, PA (US); Sayuri Smith, Dubois, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 351 days.

(21) Appl. No.: 15/504,028

(22) PCT Filed: Aug. 27, 2015

(86) PCT No.: PCT/US2015/047158
§ 371 (c)(1),
(2) Date: Feb. 15, 2017

(87) PCT Pub. No.: WO2016/033312
PCT Pub. Date: Mar. 3, 2016

(65) Prior Publication Data
US 2017/0239398 A1    Aug. 24, 2017

Related U.S. Application Data

(60) Provisional application No. 62/042,291, filed on Aug. 27, 2014.

(51) Int. Cl.
    *A61B 17/84*      (2006.01)
    *A61B 17/86*      (2006.01)
    (Continued)

(52) U.S. Cl.
    CPC ........ *A61B 17/8625* (2013.01); *A61B 17/861* (2013.01); *A61B 17/866* (2013.01);
    (Continued)

(58) Field of Classification Search
    CPC ..................................................... A61B 17/84
    See application file for complete search history.

(56) References Cited

U.S. PATENT DOCUMENTS

| | | | |
|---|---|---|---|
| 5,601,429 A | 2/1997 | Blacklock | |
| 6,358,250 B1 * | 3/2002 | Orbay | A61B 17/68 606/280 |

(Continued)

*Primary Examiner* — Nicholas W Woodall
(74) *Attorney, Agent, or Firm* — Carol A. Marmo; Eckert Seamans Cherin & Mellott, LLC

(57) ABSTRACT

The invention relates to a biodegradable, magnesium-containing bone screw for implanting into a patient body for use in medical applications, such as, orthopedic and craniofacial surgery. The bone screw has a tapered head, a threaded shaft and pointed tip. The composition of the bone screws provide for improved biodegradability and biocompatibility, and the features of the structure of the bone screws facilitates guidance and placement during implantation as well as reduces the potential for mechanical failures. Moreover, the bone screws are effective to provide targeted release of magnesium ions resulting in enhanced new bone formation.

15 Claims, 3 Drawing Sheets

(51) Int. Cl.
  *A61L 31/14* (2006.01)
  *A61L 31/02* (2006.01)
  *F16B 35/04* (2006.01)

(52) U.S. Cl.
  CPC .......... *A61L 31/022* (2013.01); *A61L 31/148* (2013.01); *F16B 35/04* (2013.01); *A61L 2300/102* (2013.01); *A61L 2300/412* (2013.01); *A61L 2400/18* (2013.01); *A61L 2430/02* (2013.01)

(56) References Cited

U.S. PATENT DOCUMENTS

| | | |
|---|---|---|
| 7,771,459 B2 | 8/2010 | Von Oepen |
| 7,785,055 B2* | 8/2010 | Dicke ................ F16B 25/0015 411/386 |
| 9,510,932 B2* | 12/2016 | Kumta .................... C22C 23/00 |
| 2005/0216016 A1 | 9/2005 | Contiliano et al. |
| 2007/0053765 A1* | 3/2007 | Warnick ............... A61B 17/863 411/378 |
| 2008/0269810 A1* | 10/2008 | Zhang ................ A61B 17/7001 606/305 |
| 2009/0131540 A1* | 5/2009 | Hiramoto .............. A61L 31/148 514/769 |
| 2012/0010659 A1 | 1/2012 | Angert et al. |
| 2013/0022427 A1 | 1/2013 | Yamanaka et al. |
| 2014/0065009 A1* | 3/2014 | Imwinkelried ........... C22F 1/06 420/405 |
| 2017/0239386 A1* | 8/2017 | Shanov ................ A61L 27/047 |

\* cited by examiner

MAGNESIUM ENHANCED/INDUCED BONE FORMATION

CROSS-REFERENCE TO RELATED APPLICATIONS

This application claims priority under 35 U.S.C. § 119(e) to U.S. Provisional Patent Application Ser. No. 62/042,291, filed Aug. 27, 2014, entitled "Magnesium Enhanced/Induced Bone Formation", which is herein incorporated by reference.

GOVERNMENT SUPPORT AND FUNDING

The invention was made with government support under ERC-0812348 awarded by the National Science Foundation. The government has certain rights in the invention.

FIELD OF THE INVENTION

The invention relates to biodegradable bone screws composed of magnesium-containing material, e.g., pure magnesium or magnesium alloy, which are suitable as implant devices into a patient body for medical applications, such as, orthopedic, craniofacial and cardiovascular surgery.

BACKGROUND OF THE INVENTION

Bone fractures are an extremely common injury, with an estimated more than 6 million occurring each year in the United States and causing over 1 million hospitalizations annually. Fractures can arise from a wide variety of causes, such as accidents, sports and falls, as well as from pathological causes, such as, low bone density and osteoporosis resulting from age and obesity. Due to the high prevalence of these risk factors, incidences of fractures are projected to rise. Over one third of fractures require internal fixation devices to provide stabilization during healing.

Metallic implant devices, such as plates, screws, nails and pins, constructed of stainless steel, cobalt-chromium and titanium alloys are commonly used in the practice of orthopedic, craniofacial and cardiovascular implant surgery. These materials exhibit good biomechanical properties, but are not degradable over a period of rime. Thus, when the implant device is no longer needed, surgery is required for its removal. To reduce the need for surgery and risks associated therewith, it is a desire in the art to design and develop new biomaterials that are capable of degrading, e.g., dissolving, over time such that surgical removal is precluded. For example, polymers, such as polyhydroxy acids, polylactic acid (PLA), polyglycolic acid (PGA), and the like, are useful for the construction of implant devices. These materials, however, have been found to exhibit relatively poor strength and ductility, and have a tendency to react with human tissue resulting in limited bone growth. As a result, magnesium alloys have emerged as a new class of biodegradable materials for orthopedic applications. These materials exhibit properties comparable to natural bone, are non-toxic and capable of degrading, e.g., corroding, over time in a physiological environment, e.g., a patient body. In particular, magnesium degrades to produce a soluble, non-toxic corrosion hydroxide product which is harmlessly excreted through urine. To date, magnesium alloys have demonstrated the ability to regenerate both hard and soft musculoskeletal tissues, which is particularly valuable for engineering craniofacial degradable implants.

There are, however, disadvantages associated with bone screws composed of magnesium-containing material, e.g., magnesium alloy. For example, magnesium is generally a softer material than metal materials, e.g., stainless steel or titanium, conventionally used for implant devices. As a result, magnesium alloy bone screws have been found to be more prone to breakage. In certain instances, during the process of implantation, the heads of the magnesium alloy screws have sheared off, and the screws have been shown to be difficult to place in existing bone, e.g., difficult to align with a corresponding opening which is drilled into existing tissue in a patient to receive the screw. FIG. 1 is a schematic showing a bone screw 1 in accordance with the prior art. The bone screw 1 includes a head 3 having an upper surface 5, a lower surface 7 and a thickness 6 extending between the upper and lower surfaces 5,7. An indentation 9 is diametrically formed within the head 3, which extends along the entire, or nearly the entire, diameter 11 thereof. The indentation 9 is typically sized to accommodate a driver mechanism (not shown) for rotating and guiding the bone screw 1 for implantation. Extending from the lower surface 7 is an elongated shaft 13 having a straight thread form. Extending front an end 15 of the threaded shaft 13 is a tip 17. As shown, the diameter 11 of the upper surface 5 is equal to the diameter 11 of the lower surface 7.

There is a need in the art to design and develop bone screws having suitable corrosion resistance, biodegradability and biocompatibility, while having an improved design structure so as to facilitate alignment and placement of the screws, and to demonstrate minimal breakage, e.g., of the screws's head, during implantation. Furthermore, there is a desire to design and develop bone screws that degrade in vivo causing a release of magnesium ions without negatively impacting fixation or stabilization of the bone. It is believed that this release of magnesium ions in a specific location may be effective to stimulate localized bone formation and to enhance osteointegration and healing.

SUMMARY OF THE INVENTION

In an aspect of the invention, a biodegradable, magnesium-containing bone screw, is provided. The bone screw includes a head having a top surface, a bottom surface and a tapered thickness extending between the top and bottom surfaces; a shaft having a first end and a second end, the first end coupled to the bottom surface of the head, and a length linearly extending between the first and second ends, the length having a threaded form; and a pointed tip extending from the second end of the shaft.

The top surface of the head can include an indentation formed therein sized to accommodate a driver mechanism for guiding and rotating the bone screw. In certain embodiments, the indentation can extend along a diameter of the head.

The threaded form of the shaft can include a tapered thread profile. Further, the threaded form can have a thread angle from about 25 to about 75 degrees. In certain embodiments, the threaded form can have a thread angle from about 45 to about 60 degrees.

The head and shaft can be cylindrical in shape, the tip may be cone-shaped, and the top surface of the head can have a diameter that is larger than the diameter of the bottom surface.

The bone screw may be employed as an implant device for medical applications. In certain embodiments, the bone screw is employed in medical applications selected from craniofacial, orthopedic, dental and cardiovascular surgeries.

In another aspect of the invention, a method of preparing a biodegradable, magnesium-containing bone screw is provided. The method includes preparing a magnesium-containing composition, melting the magnesium-containing composition at an elevated temperature, introducing the magnesium-containing composition from step (b) into a mold, cooling and solidifying the mold. The mold includes a head having a top surface, a bottom surface and a tapered thickness extending between the top and bottom surfaces; a shaft having a first end, the first end coupled to the bottom surface of the head, a second end and a length linearly extending between the first and second ends, the length of the shaft having a threaded form; and a pointed tip extending from the second end of the shaft.

In still another aspect of the invention, a method of employing a biodegradable screw as a medical implant device in a patient is provided. The method includes preparing a magnesium-containing bone screw in accordance with the above-described method, forming an opening in existing bone in the patient, and implanting the bone screw into the opening in the existing bone of the patient. The bone screw is effective to provide targeted release of magnesium ions resulting M enhanced new bone formation.

The existing bone may be selected from craniofacial bone, orthopedic bone and dental bone.

In certain embodiments, the medical implant device further includes a fixation plate.

BRIEF DESCRIPTION OF THE DRAWINGS

A further understanding of the invention can be gained from the following description of the preferred embodiments when read in conjunction with the accompanying drawings.

DETAILED DESCRIPTION OF PREFERRED EMBODIMENTS

Figure 1:
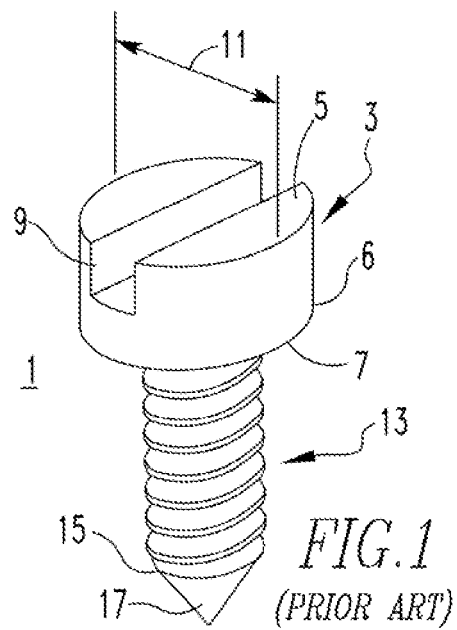
FIG. 1 is a schematic showing a bone screw, in accordance with the prior art.

The invention relates to novel, biodegradable hone screws constructed from magnesium-containing material, e.g., pure magnesium or magnesium alloy. These hone screws are suitable for implanting into a body of a patient for medical applications, such as but not limited to, orthopedic, craniofacial, dental and cardiovascular surgeries. Further, the bone screws degrade in vivo causing a release, e.g., targeted release, of magnesium ions without negatively impacting fixation or stabilization of the bone. Without intending to be bound by any particular theory, it is believed that this release of magnesium ions may be effective to stimulate localized bone formation and to enhance osteointegration and healing. Furthermore, the invention relates to novel, biodegradable bone screws having an improved structure which is designed to facilitate alignment and placement, and reduce breakage of the bone screw, e.g., head, during implantation.

A wide variety of magnesium-containing materials may be employed to construct the biodegradable bone screws of the invention. In certain embodiments, the bone screws are constructed or composed of pure magnesium, Mg. In other embodiments, the bone screws are constructed or composed of magnesium alloy. The alloying components or elements in the magnesium alloy can vary and may be selected from those known in the art. As used herein and the claims, the term "magnesium-containing materials" refers to pure magnesium and magnesium-based alloys and compositions. Non-limiting examples of suitable magnesium alloys include those described in. PCT Application having International Application No. PCT/US2012; 058939 entitled "Biodegradable Metal Alloys" filed on Oct. 5, 2012 and based on U.S. Provisional Patent Application 61/544,127 entitled "Biodegradable Metal Alloys" filed on Oct. 6, 2011; and U.S. patent application Ser. No. 14/045,011 entitled "Biodegradable Iron-Containing Compositions, Methods of Preparing and Applications Therefor" filed on Oct. 3, 2013, which are incorporated in their entirety herein by reference.

The amount of each of the components or elements in the magnesium alloys/compositions can vary and in general, the amounts are selected such that the resulting alloys/compositions are within acceptable non-toxic limits, sufficiently biocompatible and degradable over a period of time. For example, the components or elements and their amounts may be selected such that the alloys/compositions exhibit corrosion resistance in the presence of water and body fluids which allow for suitable in vitro use in a physiological environment, e.g., patient body, and exhibit corrosion resistance with minimal or no evolution of hydrogen gas as the evolution of hydrogen, e.g., hydrogen bubbles, may cause complications in a patient body.

It is contemplated that other components may be added to the alloys/compositions provided that the non-toxicity, biocompatibility and degradability remain within acceptable limits. Acceptable non-toxic limits and time frames for degradation can vary and can depend on the particular physical and physiological characteristics of the patient, in vitro site of implantation and medical use of the device.

Suitable magnesium alloys/compositors for use in the invention may be prepared using various methods and processes. The components, e.g., magnesium and one or more of iron, manganese, calcium, zirconium and zinc, may be melted or alloyed at an elevated temperature using conventional methods known in the art. In certain embodiments, the components are alloyed using high energy mechanical alloying (HEMA), uniaxial or isostatic compaction and sintering, HEMA may be conducted under a protective atmosphere, e.g., in the presence of argon, sulfur hexafluoride and mixtures thereof, to preclude, minimize or reduce decomposition of the components in the composition. Subsequent to HEMA, amorphous films may be synthesized by pulsed laser deposition (PLD).

Further, it is known to use general casting methods and, forming and finishing processes, such as, extrusion, forging, polishing (by mechanical and/or chemical means), surface treating (to form a superficial layer), and combinations thereof, to produce the bone screws of the invention for use as implant devices. For example, a molten alloyed composition may be poured into a mold, allowed to cool and thereby solidify.

Figure 2:
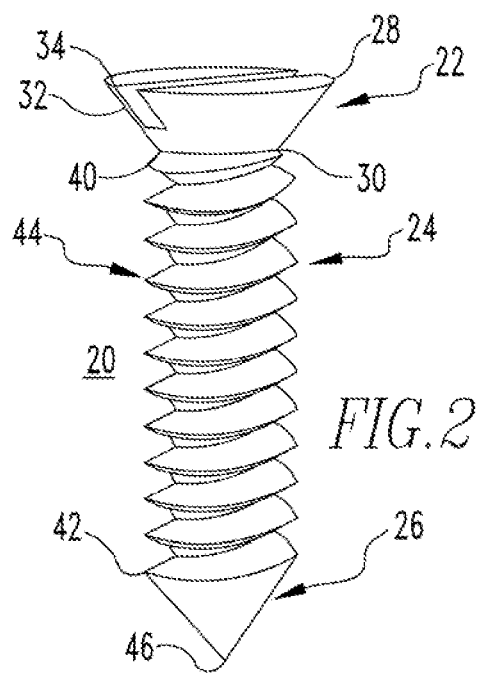
FIG. 2 is a schematic showing a bone screw, in accordance with certain embodiments of the present invention.

Suitable design structures for the bone screws can vary. FIG. 2 is a schematic showing a bone screw 20 in accordance with certain embodiments of the invention. The bone screw 20 has a head 22 a shaft 24 and a tip 26. The head 22 has a top surface 28, a bottom surface 30 and a tapered thickness 32 extending between the top and bottom surfaces 28,30. The shape of the head 22, shaft 24 and tip 26 can vary. As shown in FIG. 2, the head 22 and shall 24 are cylindrical in shape such that the top and bottom surfaces 28,30 of the head 22 are circular. The head 22 is tapered such that the top surface 28 has a greater circumference and diameter than the bottom surface 30. The top surface 28 of the head has an indentation 34 diametrically formed therein. The indentation 34 is sized, e.g., has a length and height, that is suitable to accommodate a driver mechanism (not, shown) for rotating and guiding the hone screw. In certain embodiments, the length of the indentation 34 extends along the entire or nearly the entire diameter of the top surface 28 of the head 22. It is contemplated and understood that the indentation can be formed in various shapes and sizes depending on the driver mechanism used to rotate and guide the bone screw. For example, if the driver mechanism has a Philip's head, the indentation m the bone screw head would be shaped and sized to accommodate said Philip's head. The shaft 24 has a first end 40 and a second end 42 and a length 44 linearly extending between the first and second ends 40,42. The first end 40 of the shaft 24 is coupled to the bottom surface 30 of the head 22. The length 44 includes a threaded form. The tip 26 extends from the second end 42 of the shaft 24 and has a pointed end 46. In certain embodiments, the tip 26 is cone shaped.

The threaded form of the shaft of the bone screw can have a straight thread profile or a tapered (or curved) thread profile. The angle of the threads in the threaded shaft 24 can vary. In certain embodiments, the threads are formed or positioned, such as, to have a thread angle from about 25 to about 75 degrees or from about 45 to about 60 degrees. For example, the bone screw can have a 60-degree straight thread angle, a 60-degree curved thread angle, a 45-degree straight thread angle, or a 45-degree curved thread angle.

Without intending to be bound by any particular theory, it is believed that certain thread angles, such as, the 45-degree threaded angle, can provide an increased thread pitch, which allows more threads to engage in a thin conical bone layer and this increased engagement is theoretically advantageous for screw fixation and fracture stabilization. Furthermore, it is believed that the tapered or curved thread design provides an increase in thread surface area, which can facilitate location-specific degradation and subsequent Mg ion release that may be beneficial to bone regeneration, which promotes osteointegration and local hone formation to support healing.

The bone screws 20 of the invention generally maintain fracture stability throughout healing, while degrading slowly and safety, and cause Mg ion release to enhance bone formation. The bone screws 20 are self-tapping and can include a tapered head as shown in FIG. 2) and a tapered or curved thread profile or form, as compared to conventional bone screws that are known in the art.

In certain embodiments, the bone screws of the invention are implanted into a patient body by forming one or more openings in existing bone and inserting or implanting the bone screws within the opening(s). Mg ion release into the existing bone can be exhibited by the entire bone screw overall and, more particularly, by specific parts and portions of the screw.

Figure 3:
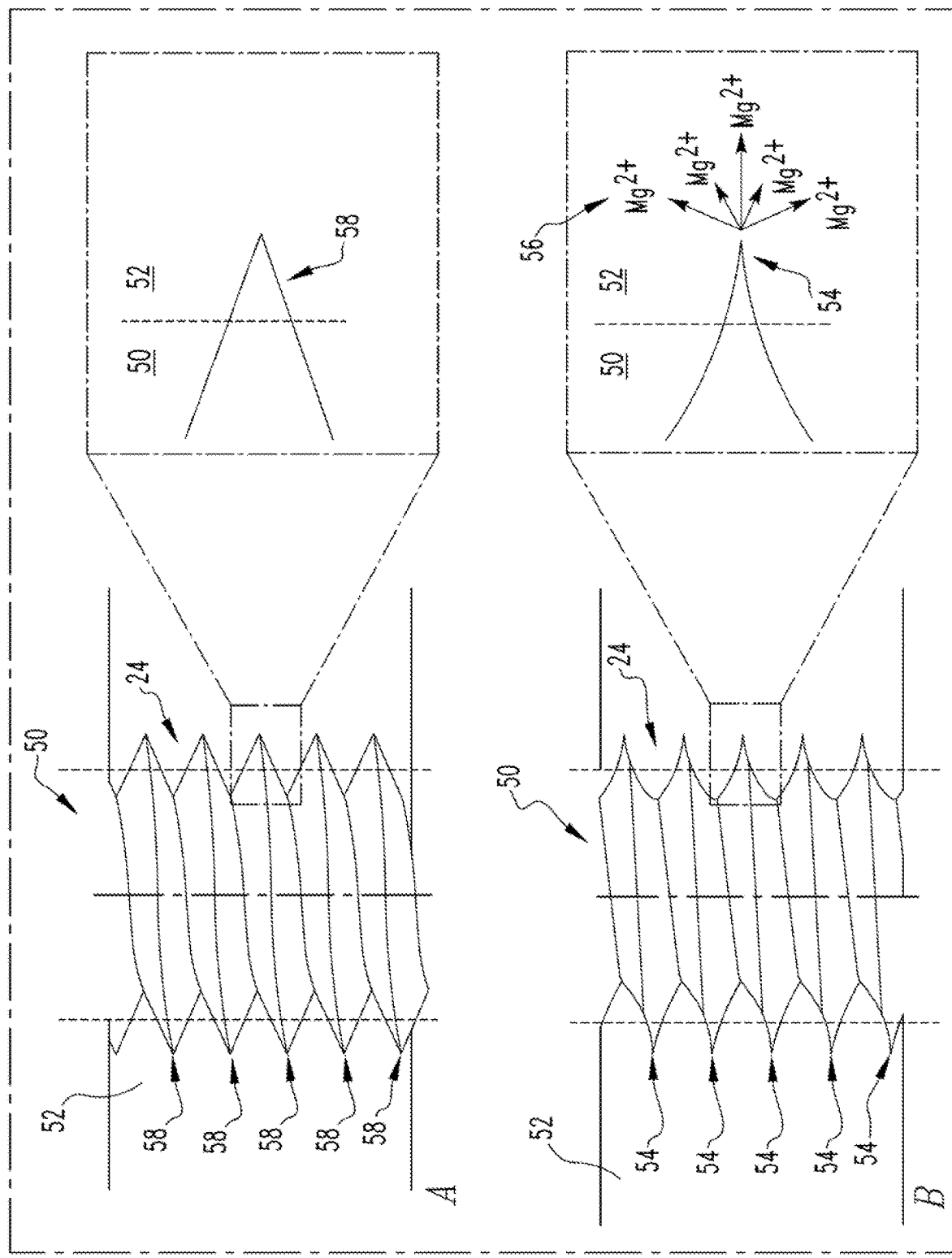
FIG. 3 is a schematic showing implantation of a bone screw having a straight thread profile (i.e., View A) and a tapered thread profile (i.e. View B), accordance with certain embodiments of the invention.

FIG. 3 is a schematic showing a threaded shaft of a bone screw inserted into a pre-drilled hole 50 of a cortical bone 52. The upper View A of FIG. 3 shows a threaded shaft 24 having a straight thread profile and the lower View 13 in FIG. 3 shows a threaded shaft 24 having a tapered (or curved) thread profile. As shown in the View B, the tapered thread profile includes a plurality of thin extensions 54 that protrude into the cortical bone 52. In accordance with the disclosed concept, it is contemplated that the plurality of thin extensions 54 will rapidly degrade in vivo and will cause a targeted or localized release, e.g., burst, of Mg ions 56 into the bone 52, as shown in View B of FIG. 3. As shown in View A, the straight thread profile also has a plurality of extensions 58 that protrude into the cortical bone 52. However, the plurality of extensions 58 do not taper (or curve) to form extensions that are as thin as the plurality of thin extensions 54 shown for the tapered thread profile in View B.

Without intending to be bound by any particular theory, it is believed that the tapered or curved thread form provides early, location-specific degradation at the thread extensions (thread tips) causing Mg Ion release to stimulate local bone formation. In this manner, bone growth can be directed inward toward the screw, as it degrades. The thin thread extensions (thread tips) will be more rapidly degraded in vivo, and will cause a burst release of Mn ion that can stimulate localized bone formation to enhance osteointegration and healing, without compromising, fixation or stabilization.

Figure 4:
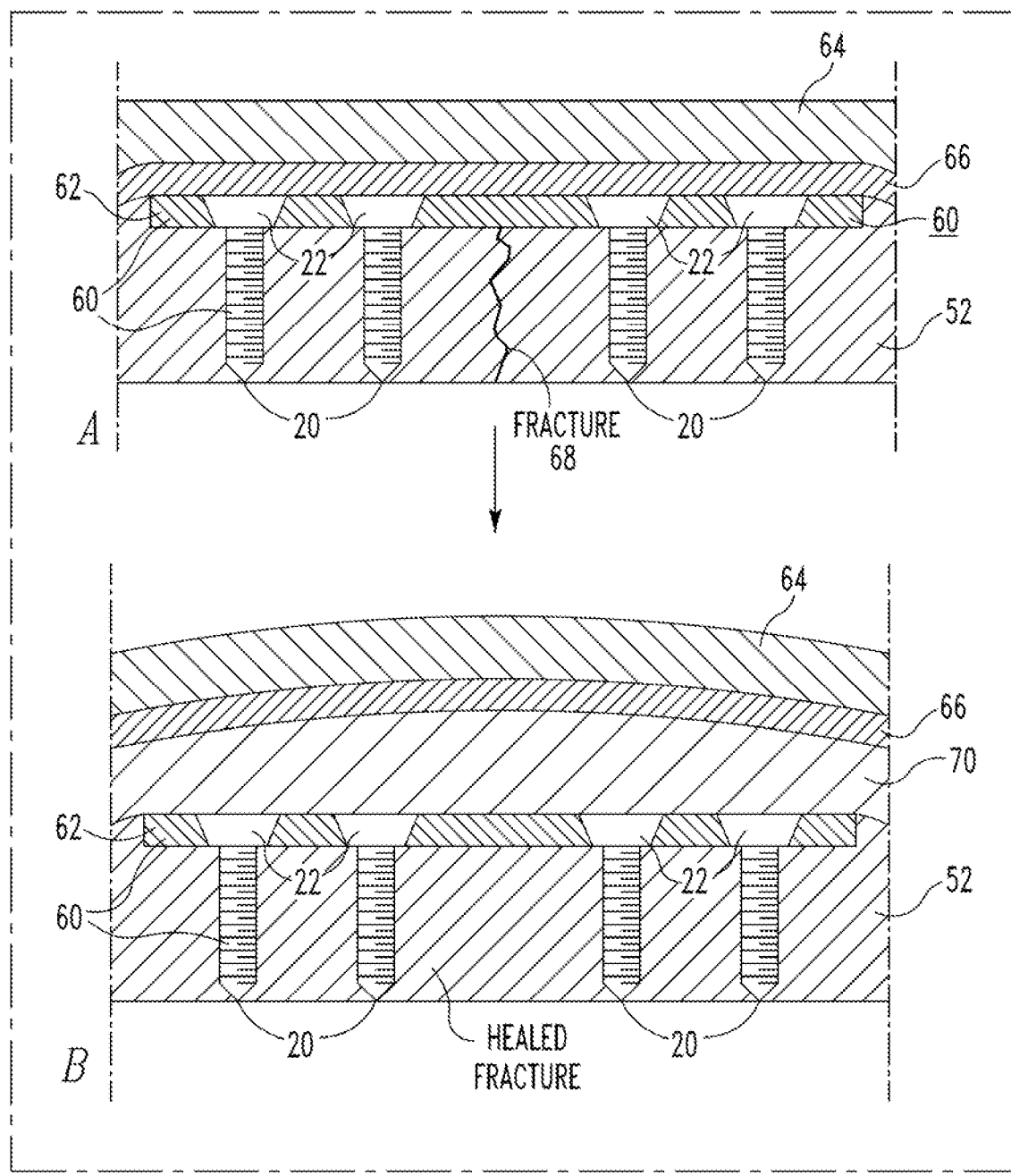
FIG. 4 is a schematic showing a combination of a plurality of bone screws and a fixation plate, in accordance with certain embodiments of the invention.

The bone screws, in accordance with the invention, may be used independently or they may be used in conjunction with fixation plates. In certain embodiments, the magnesium-containing bone screws in conjunction with a magnesium-containing fixation plate are effective to regenerate bone, FIG. 4 is a schematic that shows an implant device 60 that includes a plurality of the bone screws 20 (shown in FIG. 2) used in conjunction with a bone fixation plate 62. As shown in FIG. 4, the plurality of the head 22 of the bone screws 20 can countersink into the bone fixation plate 62, such as to reduce the overall profile of the implant device 60. Further, as shown in FIG. 4, the combination of the plurality of bone screws 20 and the bone fixation plate 62 is implanted beneath muscle 64 and periosteum 66 into the cortical bone 52 (as shown in FIG. 3). FIG. 4 shows one fixation plate with four bone screws. However, it is contemplated and understood that the number of bone screws may vary and can be more or less than four. As shown in the upper View A of FIG. 4, there is a fracture 68 in the cortical bone 52. As compared to View A, the lower View B demonstrates the mechanism of magnesium-stimulated bone formation in accordance with the invention. As shown in View B, a portion of the plurality of bone screws 20 and bone fixation plate 62 are degraded, the fracture 68 is absent, e.g., healed, and new bone 70 is formed.

It is contemplated that the bone screws in accordance with the invention are useful in a wide variety of applications including, but not limited to, craniomaxillofacial and orthopedic applications. As described, the bone screws can be used in conjunction with fixation plates. Further, the bone screws can be used for fixation of other materials and devices conventionally used for bone augmentation, such as, but not limited to, meshes and membranes.

EXAMPLES

Example 1

1. Overview

A thorough assessment of the degradation behavior and biological effect of Mg fixation devices was conducted. Specifically, there was designed and tested Mg fixation plates and screws in a rabbit ulna fracture model. Results confirmed new bone formation around Mg devices, especially above the devices where the periosteum and muscle tissue were present. In addition, there was observed no inhibition of fracture healing Mechanical testing demonstrated that healed fractures fixed with Mg devices responded similarly to health controls when subject to three point bending. Taken together, these data demonstrate the efficacy of Mg fixation devices in a load bearing fracture site.

2. Materials and Methods 2.1. Device Design and Development

Fixation devices, in accordance with the invention (and as shown in FIGS. 2 and 4), were machined with 99.9% pure Mg (Goodfellow, Coraopolis Pa.). Prior to implantation, the devices were cleaned by sonicated washes in pure acetone and ethanol, followed by sterilization with gamma radiation ($2 \times 10^6$ cGy, 23.5 Gy/min, cesium 137 source, Mark 168. J L Shepherd and Associates, San Fernando. Calif.).

2.2. In Vivo Implantation.

Prior to surgery, animals were anesthetized and forearms were shaved and disinfected. A 2 cm incision was made over the ulna. Overlying skin and muscle was carefully retracted to expose the ulna. A complete ulnar osteotomy (0.5-1 mm thick) was created using a hand held drill. A fixation device consisting of one plate and four screws was then placed to stabilize the fracture. The incision was closed in layers with sutures and left un-casted. Animals were monitored daily for general behavior, movement, and food and water intake. In addition, forearms were checked thoroughly by visual inspection and gentle palpation for signs of infection or subcutaneous gas pocket formation. Observable gas pockets were removed with a sterile syringe. All gas pocket formations and removals were documented.

2.3. X-ray Imaging.

X-ray imaging was used to monitor device placement and fracture healing. All animals received x-rays in following surgery and every two weeks thereafter.

2.4. Three Point Bend Test.

A three point bend test was used to evaluate the relative strength of the ulnae after 16 weeks. Prior to testing, forearms were carefully dissected and overlaying soft tissue Was removed. For all samples, the radius and ulna were fused, preventing us from accurately separating the bones for testing. To, exclude radial contributions from the test, two transverse cuts were created on either side of the fracture site and remaining device (4 cm apart) using a low speed saw and diamond blade (Buehler USA, Lake Bluff, Ill.) as previously described. An Instron 5564 (Instron USA, Norwood, Mass.) with 2 kN load capacity was used for testing. For each sample, the radius and ulna were positioned on the same horizontal plane on two lower stabilizing points positioned 5 cm apart. The fracture site and radial cuts were centered within these points. One upper moving point was positioned at the center of the two lower points. Test parameters were modified from previous studies, including a 1 N pre-load, loading speed of 5 mm/min, and stop point of 0.5 mm flexural extension (previously determined to be non-destructive). The flexural load at 0.5 mm extension was recorded for each sample. Intact ulnae were similarly prepared and used as healthy controls.

2.5. MicroCT Analysis.

High resolution microCT was used to evaluate device degradation and new bone formation. Devices were scanned before implantation with a VivaCT40 (Scanco Medical AG, Bruttisellen, Switzerland) and 10.5 µm voxel size (55 kV, 72 µA), In addition, devices were scanned after eight and 16 weeks (n=4 per time point) using a SkyScan1172 (Bruker-MicroCT, Kontich, Belguim) scanner with a 10 µm voxel size, 79 kV tube potential and 125 µA tube current. 3D volumes of the scanned samples were generated from acquired 2D lateral projections using Reconn software (Bruker-MicroCT, Kontich, Belgium). For analysis, scanned bone volumes were digitally reoriented using the SkyScan DataViewer software, and user-defined remaining Mg and corrosion product regions of interest were generated using the SkyScan CTAn software (version 1.13.5.1) as previously described. Mg devices were segmented from surrounding soft and hard tissues based on the absorption coefficient (equivalent to mineral density) of remaining Mg and corrosion product. The relative x-ray absorption coefficients within each of these two layers were distinctly different, generating a clear interface between the two, as well as between the corroded product and background. These interfaces were identifiable as inflection points within the distribution of mineral densities histogram from a region of interest including both remaining Mg and corrosion product. These inflection points were used to define thresholds for the Mg and corrosion product, and were verified by visual inspection.

Following segmentation, volume quantifications were obtained to evaluate device degradation and bone formation. Corrosion rate was calculated through the microCT-evaluated Mg volume kiss using Equation 1, where CR is corrosion rate in mm/yr, delta V is change in Mg volume in $min^3$, A is surface area in $mm^2$, and t is time in years. Devices were considered in their entirety, and also divided into head and shaft regions with respective regions of interest defined. The head region was defined as any area of the screw above the bottom edge of the plate, while the shaft region was defined as any area of the screw below the bottom edge of the plate.

In addition to device volume change, new bone formation around the devices, as well as bone-device contact was assessed through micron's. New bone around the devices was defined as any bone above the bottom of the plate. Importantly, this region originally contained only muscle and soft tissue; therefore, any bone observed within this region was newly formed. Bone contact throughout the screw shafts was calculated as the intersection surface area between Mg and bone using CTAn.

$$CR = \text{delta } V/(At) \qquad \text{Equation 1:}$$

2.6. Histological Processing.

Samples were formalin fixed and embedded in Technovit 9100 New® (Heraeus Kulzer, Hanau, Germany). Samples were sectioned and stained with Toluidine Blue to visualize bone morphology at the fracture site, device-tissue interface, and within areas of newly formed bone.

2.7. Statistical Analysis.

Statistical analysis was performed using IBM SPSS Statistics 19 (IBM, Armonk, N.Y.).

3. Results 3.1. Mg Devices did not Cause Adverse Health Events.

All devices were well tolerated by the animals. Immediately following surgery, the animals resumed normal movement and behavior, including weight bearing on both forearms.

3.2. Mg Device Underwent Gradual Degradation Accompanied by Corrasion Product Formation and Gas Formation.

Initial evidence of device degradation was observed through subcutaneous gas pocket formation. Subcutaneous gas pocket formation was not observed in all animals. Less than 20% of animals developed a subcutaneous gas pocket over the implant site which was easily removed with a sterile syringe without causing infection or interference with healing. Pockets consisted of gas without additional blood or fluid. Gas pocket formation was observed through five weeks post-operative. The largest number of removals, three, was performed during the second week, with all other weeks only requiring one removal each. No gas pocket formation was observed after five weeks post-operative.

High resolution microCT was used to study device degradation (n=8 screws, n=2 plates). Based on distinct material density differences, volumes of Mg and corrosion product were quantified separately. Volume quantification revealed a net loss of volume for Mg screws after eight weeks. Mg volume was reduced by 4.41±0.49 mm$^3$ after eight weeks. Meanwhile, 3.35±0.60 mm$^3$ of corrosion product was produced at the surface. Based on this change. In Mg volume, the in vivo corrosion rate of the Mg screws was calculated to be 0.40±0.04 mm/year. Corrosion behavior varied between different regions of the screws. After eight weeks, the screw head region consisted of 47.09±13.76 volume percent of Mg, and 52.91±13.76 volume percent of corrosion product. In contrast, the screw shaft region consisted of 75.04±3.34 volume percent of Mg, and 24.96±3.34 volume percent of corrosion product. Similar to the screws, Mg plate volume was reduced after eight weeks. Specifically. Mg plates corroded at a rate of 0.55±0.02 mm/year, resulting in 19.57±0.66 mm$^3$ of Mg volume loss after eight weeks. Due to extensive corrosion product formation and integration with surrounding tissues, accurate device volume quantification after 16 weeks was not possible. However, additional Mg volume loss and corrosion product production was observed.

3.3. Fracture Healing was Uninhibited by Degrading Mg Devices.

Bi-weekly x-rays showed progressive healing throughout the study. These observations were confirmed by microCT and histological staining after eight and 16 weeks. After eight weeks, fracture healing was observed as proximal and distal cortical bone union for most samples. After 16 weeks, more mature healing was observed, with full thickness cortical hone bridging at the fracture site. Histological staining showed normal bone morphology within these regions including osteocytes and osteoid.

3.4. Bone-Device Contact Prevalent Despite Ongoing Device Degradation.

Bone device contact was observed through microCT and histological staining. In the presence of ongoing corrosion, high levels of bone-device contact were observed after eight and 16 weeks in vivo. Areas of bone-device contact were more prevalent in slower degrading regions, such as around the plate and screw heads. New bone growth was often observed around the screw head and within the driver slot, with direct bone-device contact. Bone device contact along screw shafts were quantified after eight weeks, revealing over 25% of the screw shaft surface area in contact with bone.

3.5. Abundant Bone Growth Observed Over and Around Degrading Mg Devices.

New bone was formed over and around all Mg devices. This bone formation was observed throughout the study by x-ray, and was further assessed by microCT and histological staining after eight and 16 weeks. After eight weeks, new bone partially covered all Mg devices. After 16 weeks, this new bone completely covered all Mg devices. MicroCT was used to quantify the amount of new bone formed over the fixation devices. A significant increase in overlaying bone formation was observed from eight to 16 weeks (p–0.001), with 100.20±33.80 mm$^3$ of new bone formed within this period.

3.6. Forearm Structural Properties Maintained after 16 Weeks.

The relative structural properties of the healed ulnae was assessed by three point bend testing after 16 weeks. Bone overgrowth and degraded fixation devices were left in place for testing; therefore, results reflect the entire bone-device complex as it would be loaded in viva. Bend test results revealed a slight, though not significant, increase in flexural load for healed ulnae fixed with Mg devices compared to intact ulnae controls.

4. Discussion

The efficacy of degradable Mg fixation plates and screws in a loaded ulna fracture model was assessed. The results demonstrated abundant new hone formation around degrading Mg devices. The effect of Mg on fracture healing and hone formation was evaluated. A thorough investigation of 99.99% Mg fixation plates and screws was conducted to confirm that these degradable devices facilitate fracture healing, while stimulating local bone formation.

As Mg degrades, hydrogen gas is produced. Depending on the implant's local environment and available blood flow, this gas may be cleared from the implant site without accumulation. However, rapid corrosion rate and/or insufficient gas removal may lead to accumulation. Only a small number of gas pockets were observed, indicating that most gas released during device degradation was efficiently cleared from the implant site. Furthermore, observed gas pockets did not disrupt fracture healing, bone formation, or surrounding tissue health.

In addition to hydrogen, degrading Mg typically produces corrosion product on its surface. The material properties of the remaining Mg and corrosion product are not equal, and therefore do not provide equal contributions to device function. For these reasons, device degradation was assessed in terms of Mg volume loss and corrosion product volume gain. A net volume loss for all devices was observed with considerable corrosion product formation. A greater corrosion rate for the plates than the screws (0.55±0.02 and 0.40±0.04 mm/year, respectively) was also observed. This difference was likely attributed to the devices' local environment. Unlike the screws, which were largely contained within bone, the plates were initially covered by muscle. This tissue has a higher Water content and blood flow than bone, and therefore likely accelerated plate corrosion. In addition, it was likely that areas of contact between the plate and ulna further enhanced plate corrosion.

Also observed were differences in corrosion behavior between portions or regions of the screws. Specifically, the data suggested that corrosion was enhanced for screw heads compared to shafts. The screws were tested as part of a fixation system, and therefore screw heads were in contact with overlaying soft tissue, as well as the fixation plate. Shearing of these components, as well as compression during loading, likely contributed to corrosion within the head region. Despite these observations of accelerated corrosion, all devices remained in place and provided sufficient stabilization throughout the evaluation. Furthermore, high levels of bone-device contact were observed, revealing osteointegration of the devices.

In the presence of ongoing device corrosion, fracture healing remained uninhibited, and cortical bone union matured throughout the evaluation. Mature healing was observed after eight weeks. These results demonstrated the ability of Mg fixation devices to facilitate physiological healing and long-term remodeling in a loaded fracture environment. This reflects a unique advantage of Mg devices over resorbable polymer devices, which are often not suitable for load bearing application.

Mg devices can, not only facilitate fracture healing but also can enhance bone formation. Abundant bone formation over and around all degrading Mg devices was observed. This bone formation occurred over the devices, where periosteal and muscle tissue layers are typically present. It was demonstrated that prolonged exposure to Mg degradation can cause progressive bone formation. This bone formation was not typically seen with resorbable polymer or permanent metal devices, and therefore highlights a unique advantage of Mg fixation devices. In this manner, the degrading fixation device is gradually replaced b bone, without compromising fracture healing.

As these devices degraded, Mg was released, and local cells were stimulated to form bone. Considering the location of the newly formed bone observed, it is likely that the periosteum served as a cell source for osteogenic differentiation. Cells within this tissue layer, including osteoblasts and pluripotent mesenchymal stem cells, are known to facilitate bone growth and repair. It is also likely that Mg released from the degrading devices stimulated stem cells within the periosteum to initiate bone formation over the devices. This bone formation then continued as device degradation, and subsequent Mg release, persisted over time.

This new bone may have contributed to the structural properties of the ulna, helped provide stabilization, and facilitated weight-bearing activity during healing. Through three point bend testing, there was observed a similar flexure load response of healed ulnae when compared to healthy, un-fractured controls. These results revealed that the structural properties of healed bone are similar to native ulnae, and that functional regeneration occurred.

5. Conclusion

The efficacy of degradable Mg fixation plates and screws in a loaded rabbit ulna model was evaluated. It was demonstrated that 99.9% Mg fixation devices underwent localized corrosion in a primarily honey environment, with increased corrosion in the screw head region compared to the shaft region. It was shown that Mg device degradation did not inhibit fracture healing, and enhanced local bone formation around the devices. Furthermore, it was shown that the structural properties of the healed bone after 16 weeks were not compromised. These biological and mechanical results demonstrate the potential use of Mg alloys as fracture fixation devices.

Example 2

1. Overview

The novel fixation devices (as shown in FIGS. 2 and 4) were subjected to in vivo testing using a rabbit ulna fracture model. Devices were implanted to provide stabilization to complete ulnar osteotomies and assessed after eight and 16 weeks post-operative.

2. Ease of Insertion

Some damage occurred during implantation of the Mg devices. The damage may have been due to Mg's relatively low stiffness when compared to titanium, and inconsistencies in ulnar thickness. More likely, device damage was the result of applying excessive torque during implantation or irregularities within the material itself. During in vivo surgeries, surgeons reported that screws with the novel tapered (curved) thread form were easier to implant, requiring less torque and breaking less frequently when compared to screws with a traditional thread form. On average, screws with a traditional thread form were twice as likely to be damaged during implantation when compared to screws with the novel tapered (curved) thread form.

3. Device Degradation

Device degradation was observed through high resolution microCT. Density differences in underlying Mg and newly formed corrosion product could be observed visually and quantified using threshold-based analysis. Underlying Mg and corrosion product were quantified separately for traditional (straight) and novel tapered (curved) threaded screws within both the head and shaft regions. No significant differences were observed in the overall degradation behavior of the novel tapered (curved) screws compared to traditional designs, suggesting an adequate volume for stabilization was maintained.

4. Fracture Healing

Biweekly in vivo x-rays show ongoing fracture healing in the presence of device degradation throughout the course of the evaluation. In addition, microCT 2D slices showed union of proximal and distal cortical bones at the fracture site after eight and 16 weeks. MicroCT and histological staining showed further detail of fracture healing. MicroCT slices showed cortical bone union after eight weeks with further maturation after 16 weeks. High magnification images of Toluidine stained sections showed normal bone morphology within the healed cortical bones at the fracture site after eight and 16 weeks. High levels of bone-device contact were observed around degrading Mg devices, indicating good osteointegration, which supports device stabilization. Areas of bone-device contact were observed after eight and 16 weeks. Interfaces of Mg devices and bone were observed through microCT. A longitudinal slice of a Mg plate and screw showed areas of bone contact around the screw head, shaft, and plate edge. A transverse slice of a Mg screw shaft showed bone contact around screw perimeter after 16 weeks. Toluidine Blue showed bone morphology at bone-plate interface after eight weeks.

5. New Bone Growth

Abundant new bone growth was observed around degrading devices after eight and 16 weeks post-operative. After eight weeks, partial bone covering was observed over all devices, with complete bone overgrowth observed after 16 weeks. The volumes of bone overgrowth were quantified at both time points, and a significant increase in bone volume was determined. Toluidine Blue histological stain showed normal bone morphology with osteocytes and osteoid within the newly formed bone. New bone overgrowth was quantified using microCT. Conservatively, bone above the plate baseline was identified as new bone. A significant increase in bone was observed from eight to 16 weeks.

6. Structural Integrity

The structural properties of healed forearms were assessed using three point bend tests. Overlying tissue was carefully dissected to eliminate its mechanical contribution. Ulnae were stabilized on two points and subject to a small displacement (0.5 min) from a central, top point. The resulting load was recorded and average max force at max displacement was plotted. Results showed no significant difference between material and/or screw design.

7. Conclusion

The efficacy of the novel fixation devices was assessed using a rabbit ulna fracture model. Results showed gradual device degradation over time, without interference on fracture healing or new bone formation. There was demonstrated the positive effect of Mg degradation on local bone formation with progressive increase in overlying bone from eight to 16 weeks post-operative. Mechanical testing showed that the structural properties of the healed ulnae were comparable to healthy, un-fractured controls after 16 weeks post-operative.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

We claim:

1. An osteo-regenerative, biodegradable, magnesium-based bone screw (20) implant, comprising:
   a magnesium-based alloy;
   a head (22) having a top surface (28), a bottom surface (30) and a thickness (32) extending between the top and bottom surfaces (28,30);
   a threaded shaft (24) having a first end (40) coupled to the bottom surface (30) of the head (22), a second end (42) and a vertical length (44) linearly extending between the first and second ends (40,42), comprising:
      a plurality of threads, each of the plurality of threads comprising:
         a continuous upper surface;
         a continuous opposite lower surface,
      wherein the continuous upper surface of each of the plurality of threads has a concave curve towards the continuous lower surface of each of the plurality of threads and the continuous lower surface of each of the plurality of threads has a concave curve towards the continuous upper surface of each of the plurality of threads, and
      a circumferential, tapered thread edge comprising a pointed thin extension formed by the continuous upper surface and continuous opposite lower surface of each of the plurality of threads,
   wherein the pointed thin extension of each of the plurality of threads has biodegradation and osteo-regenerative properties, and is configured to interface with the patient's bone or bone tissue that is targeted for local bone regeneration; and
   a pointed screw tip (26) extending from the second end (42) of the threaded shaft (24),
   wherein the concave curve of each of the upper and lower surfaces of the plurality of threads is configured to rapidly disperse Mg ions in vivo to stimulate bone growth into the screw faster to promote healing.

2. The bone screw (20) of claim 1, wherein the thread profile has a thread angle from about 25 to about 75 degrees.

3. The bone screw (20) of claim 2, wherein thread profile has a thread angle from about 45 to about 60 degrees.

4. The bone screw (20) of claim 1, wherein the head (22) and the threaded shaft (24) are cylindrical in shape, the screw tip (26) is cone-shaped, and the top surface (28) of the head (22) has a diameter greater than the diameter of the bottom surface (30).

5. The bone screw (20) of claim 1, wherein the top surface (28) of the head (22) has an indentation (34) diametrically formed therein sized to accommodate a driver mechanism for guiding and rotating the bone screw (20).

6. The bone screw (20) of claim 1, wherein said implant device is selected from the group consisting of craniofacial, dental, orthopedic and cardiovascular medical implant devices.

7. The bone screw (20) of claim 1, wherein adjacent threads in the plurality of threads form a concave indentation such that an outer edge of the thread profile comprises a plurality of concave indentations in a vertical direction.

8. A method of preparing an osteo-regenerative, biodegradable, magnesium-based bone screw (20), comprising:
   (a) preparing a magnesium-based alloy;
   (b) melting the magnesium-based alloy at an elevated temperature;
   (c) introducing the magnesium-based alloy from step (b) into a mold, the mold comprising:
      a head (22) having a top surface (28), a bottom surface (30) and a thickness (32) extending between the top and bottom surfaces (28,30);
      a threaded shaft (24) having a first end (40) coupled to the bottom surface (30) of the head (22), a second end (42) and a length (44) linearly extending between the first and second ends (40,42), the length (44) of the threaded shaft (24) having a thread profile, comprising:
         a plurality of threads, each of the plurality of threads comprising:
            a continuous upper surface;
            a continuous opposite lower surface,
         wherein the continuous upper surface of each of the plurality of threads has a concave curve towards the continuous lower surface of each of the plurality of threads and the continuous lower surface of each of the plurality of threads has a concave curve towards the continuous upper surface of each of the plurality of threads, and
         a circumferential, tapered thread edge comprising a pointed thin extension formed by the continuous upper surface and continuous opposite lower surface of each of the plurality of threads,
      wherein the pointed thin extension of each of the plurality of threads has biodegradation and osteo-regenerative properties, and is configured to interface with the patient's bone or bone tissue that is targeted for local bone regeneration; and
      a pointed screw tip (26) extending from the second end (42) of the threaded shaft (24),
      wherein the concave curve of each of the upper and lower surfaces of the plurality of threads is configured to rapidly disperse Mg ions in vivo to stimulate bone growth into the screw faster to promote healing; and
   (d) cooling and solidifying the mold to form the bone screw (20).

9. The method of claim 8, wherein adjacent threads in the plurality of threads form a concave indentation such that an outer edge of the thread profile comprises a plurality of concave indentations in a vertical direction.

10. A method of employing an osteo-regenerative, biodegradable screw (20) as a medical implant, comprising:
   preparing a magnesium-based alloy bone screw (20), comprising:
      a head (22) having a top surface (28), a bottom surface (30) and a thickness (32) extending between the top and bottom surfaces (28,30);
      a threaded shaft (24) having a first end (40) coupled to the bottom surface (30) of the head (22), a second end (42) and a length (44) linearly extending between the first and second ends (40,42), comprising:

a plurality of threads, each of the plurality of threads comprising:
a continuous upper surface;
a continuous opposite lower surface; and
a circumferential thread edge,
wherein the continuous upper surface of each of the plurality of threads has a concave curve towards the continuous lower surface of each of the plurality of threads and the continuous lower surface of each of the plurality of threads has a concave curve towards the continuous upper surface of each of the plurality of threads to form the circumferential thread edge; and
tapering the circumferential thread edge, forming a pointed thin extension; and
a pointed screw tip (26) extending from the second end (42) of the threaded shaft (24);
forming an opening (50) in the patient's bone (52); and
implanting the bone screw (20) into the opening (50) in the patient's bone (52) to interface with the patient's bone or bone tissue that is targeted for local bone regeneration,
wherein the pointed thin extension of each of the plurality of threads protrudes into the patient's bone (52), and
wherein the concave curve of each of the upper and lower surfaces of the plurality of threads is configured to rapidly disperse Mg ions in vivo to stimulate bone growth into the screw faster to promote healing.

11. The method of claim 10, wherein the existing bone (52) is selected from the group consisting of craniofacial bone, dental bone and orthopedic bone.

12. The method of claim 10, wherein the plurality of pointed thread tips (54) degrades into the existing bone (52) causing a release of magnesium ions (56) in the existing bone (52).

13. The method of claim 10, wherein the entire medical device releases magnesium ions (56) in the existing bone (52).

14. The method of claim 10, wherein the medical device further comprises a magnesium-containing fixation plate (62).

15. The method of claim 10, wherein adjacent threads in the plurality of threads form a concave indentation such that an outer edge of the thread profile comprises a plurality of concave indentations in a vertical direction.

* * * * *